United States Patent
Barg et al.

(10) Patent No.: US 12,390,313 B2
(45) Date of Patent: Aug. 19, 2025

(54) PROCESS FOR THE PRODUCTION OF DENTAL MILLING BLANKS

(71) Applicant: VOCO GmbH, Cuxhaven (DE)

(72) Inventors: Andree Barg, Otterndorf (DE); Daniel Oldenburger, Cuxhaven (DE); Tobias Ebert, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 26 days.

(21) Appl. No.: 18/335,725

(22) Filed: Jun. 15, 2023

(65) Prior Publication Data

US 2024/0008963 A1 Jan. 11, 2024

(30) Foreign Application Priority Data

Jul. 7, 2022 (DE) ............... 10 2022 116 932.4

(51) Int. Cl.
*A61C 13/00* (2006.01)
*A61C 13/08* (2006.01)
*C08K 3/38* (2006.01)

(52) U.S. Cl.
CPC ...... *A61C 13/0022* (2013.01); *A61C 13/0006* (2013.01); *A61C 13/081* (2013.01); *C08K 3/38* (2013.01)

(58) Field of Classification Search
CPC ............ A61C 13/0022; A61C 13/0006; A61C 13/081
See application file for complete search history.

(56) References Cited

U.S. PATENT DOCUMENTS

| | | |
|---|---|---|
| 5,990,195 A | 11/1999 | Arita |
| 6,345,984 B2 | 2/2002 | Karmaker |
| 2002/0090525 A1 | 7/2002 | Rusin |
| 2002/0156152 A1 * | 10/2002 | Zhang ............... A61K 6/30 524/492 |
| 2004/0010055 A1 * | 1/2004 | Bui ............... A61K 6/887 523/116 |
| 2013/0172441 A1 | 7/2013 | Takahata |
| 2014/0162216 A1 | 6/2014 | Craig |
| 2015/0182315 A1 | 7/2015 | Okada |
| 2016/0128812 A1 | 5/2016 | Nakayama |
| 2018/0028413 A1 | 2/2018 | Craig |
| 2018/0161251 A1 | 6/2018 | Wang |
| 2018/0228580 A1 | 8/2018 | Oldenburger |
| 2018/0271629 A1 | 9/2018 | Maletz |
| 2019/0247168 A1 | 8/2019 | Oldenburger |
| 2023/0091200 A1 | 3/2023 | Zhang et al. |

FOREIGN PATENT DOCUMENTS

| | | | |
|---|---|---|---|
| CA | 235700 | * | 7/2000 |
| CA | 2382780 | * | 3/2001 |
| CN | 112494341 | | 3/2021 |
| DE | 2462271 C2 | | 5/1982 |
| JP | 2017109036 | | 6/2017 |
| JP | 2019098073 | | 6/2019 |
| JP | 2019098074 | | 6/2019 |
| WO | WO2019065777 | * | 4/2019 |

* cited by examiner

*Primary Examiner* — Edmund H Lee
(74) *Attorney, Agent, or Firm* — DUANE MORRIS LLP; Gregory M. Lefkowitz; Brandon A. Chan

(57) ABSTRACT

The present invention relates to a process for producing dental milling blanks, wherein inorganic filler powders are in a first step surface-coated with a silane and wherein in a second step a polymerizable composition is adsorbed on the silanized surface. Subsequent compression and polymerization affords a homogeneous milling blank having very good mechanical properties.

18 Claims, No Drawings

PROCESS FOR THE PRODUCTION OF DENTAL MILLING BLANKS

The present invention relates to a process for producing composite-based dental milling blanks and to the dental milling blanks produced by said process.

The invention is defined in the appended patent claims. Preferred aspects of the present invention emerge moreover from the description hereinbelow, including the examples.

Where particular configurations defined for one aspect of the invention (process, composition, milling blank or use) are described as preferred, the corresponding statements in each case apply mutatis mutandis for the other aspects of the present invention too. Preferred individual features of aspects of the invention (as defined in the claims and/or disclosed in the description) are combinable with one another and are preferably combined with one another unless in the individual case the present text indicates otherwise to the person skilled in the art.

Technical progress in computer-controlled machines has resulted in the development of milling machines capable of producing prosthetic restorations with unprecedented accuracy in the shortest time possible and with minimal effort. This is the background to the development of what is known as "digital dentistry". Today it is of paramount importance in dentistry.

In the beginning, only ceramic or metallic materials underwent milling, but advances in dental composite materials increasingly better adapted to the natural hard tooth substance led to this substance class too becoming of interest for use as milling blanks.

Composite-based dental milling blanks are known from the prior art.

DE 699 22 413 T2 describes a cuttable milling blank that contains a polymer resin and a finely divided filler material having a maximum particle diameter of less than 50 micrometers. The resin phase of the dental compositions studied in this document comprises the system bis-GMA (2,2-bis[4-(2-hydroxy-3-methacryloyloxypropoxy)phenyl] propane) and TEGDMA (triethylene glycol dimethacrylate); the filler phase comprises surface-silanized silica and glass.

EP 3 050 533 A1 discloses dental resin blocks that use as the resin phase UDMA/TEGDMA (urethane dimethacrylate/triethylene glycol dimethacrylate) 80/20, UDMA/bis-MEPP/HDP (urethane dimethacrylate/2,2-bis(4-methacryloyloxypolyethoxyphenyl)propane/2-hydroxy-1,3-dimethacryloyloxypropane 60/20/20 and 50/30/20, and UDMA/bis-MEPP (urethane dimethacrylate/2,2-bis(4-methacryloyloxypolyethoxyphenyl)propane 60/40. These resin compositions are mixed with inorganic fillers to form free-radical-curable pastes in filler to resin weight ratios of from 64:36 to 70.8:29.2 and then thermally polymerized into resin blocks using BPO (benzoyl peroxide).

DE 24 62 271 C2 claims dental shaped articles comprising at least one polymerized acrylate or methacrylate and a silanized microfine inorganic silicon dioxide-based filler that are characterized in that they contain as the polymerized acrylate or methacrylate a polymer of bis-GMA or of another bisphenol A derivative or of a reaction product of hydroxyethyl methacrylates and diisocyanates, optionally together with polymers of short-chain methacrylic esters and/or of difunctional acrylic or methacrylic esters and, as the inorganic filler, exclusively microfine silicon dioxide having a particle size of from 10 to 400 nm and having a BET surface area of less than 200 $m^2/g$ in an amount of from 20% to 80% by weight.

EP 2 623 065 B1 discloses blanks for a dental milling machine targeted at high mechanical properties such as flexural strength and gloss stability. These properties are achieved by a blank for a dental milling machine that is formed from a cured product of a curable composition and that comprises: (a) a polymerizable monomer; (b) a spherical inorganic filler having an average primary particle size of not less than 0.1 µm and less than 1 µm and (c) an inorganic ultrafine particle aggregate filler consisting of aggregates of inorganic ultrafine particles having an average primary particle size of from 2 to 50 nm. Used as the resin matrix here is a monomer mixture of bis-GMA/TEGDMA/bis-MEPP (2,2-bis[4-(2-hydroxy-3-methacryloyloxypropoxy)-phenyl]propane/triethylene glycol dimethacrylate/2,2-bis(4-methacryloyloxypolyethoxyphenyl)propane in the weight ratio 20/30/50.

WO 2011/087832 A1 is directed to thermally cured composite blanks that should have significantly improved mechanical and aesthetic properties. The free-radical-curable compositions contain initiators that decompose thermally. Because decomposition takes place at elevated temperatures, monomers are prevented from gelling prematurely under normal processing conditions and discoloring the blank through degradation processes.

WO 2016/140950 A1 describes composite materials that in the cured state can also be used as dental milling blanks. The compositions comprise a curable resin component, ceramic fibers and filler in the form of nanoclusters. The polymers should yield highly aesthetic restorations and have excellent polishability and gloss retention properties. In an exemplary embodiment, the composition of a resin phase is stated, the constituents of which bis-GMA, TEGDMA, UDMA, bisEMA-6 (ethoxylated bisphenol A dimethacrylate with 6 ethoxy groups) and PEG600DM (polyethylene glycol dimethacrylate in which the molecular weight of the polyethylene units is approx. 600 g/mol) are used in weight ratios of 25/1.2/35/35/3.8.

U.S. Pat. No. 6,345,984 B2 relates to milling blanks wherein the composite material contains a particulate filler in a size range from about 0.1 to 5.0 µm and colloidal silicate in a size of from 1 to about 70 nm and also a resin phase of ethoxylated BPA (bisphenol A) dimethacrylate and having a degree of ethoxylation ranging from 1 to 20, preferably from 2 to 7, moles of ethylene oxide/mole BPA. The milling blank overall consists of approx. 20% to approx. 30% by weight of an organic matrix and approx. 65% to approx. 85% by weight of particulate filler, wherein the organic matrix consists of approx. 65% to approx. 90% by weight of ethoxylated BPA dimethacrylate and approx. 10% to approx. 30% by weight of a methacrylate oligomer, for example a polycarbonate dimethacrylate condensation product. Taking account of U.S. Pat. No. 4,544,359, cited in U.S. Pat. No. 6,345,984 B2, the typical composition of a milling blank then appears to be as follows: particulate filler (0.1 to 5 µm) 65% to 79% by weight, colloidal silicate (1 to 70 nm) 1% to 5% by weight, and organic matrix 20% to 30% by weight.

DE 198 23 530 B4 relates to a dental resin material that is shaped into a dental prosthesis by milling and that comprises an acrylic resin polymer containing 20% to 70% by weight of an inorganic filler having an average particle size of from 10 to 40 nm in diameter, 1% to 40% by weight of a glass powder having an average particle size of from 0.1-5 µm in diameter and 1-40% by weight of an organic-inorganic composite filler produced by mixing and curing of a mixture of an ultrafine inorganic filler having an average particle size of from 10 to 40 nm in diameter and a methacrylate or acrylate monomer having at least one unsaturated double bond and pulverizing the cured mixture such that it has an average particle size of from 5 to 50 µm in diameter, wherein the acrylic resin polymer comprises a combination of a methacrylate or acrylate monomer having at least one unsaturated double bond and a thermal polymerization initiator. The composite composition of a milling blank is described in example 5. The resin phase comprises UDMA/bis-MEPP in a weight ratio of 5/20 and the solid phase contains 22% by weight of inorganic filler (for example Aerosil having an average particle size of from 10 to 40 nm), for example OX-50 (having a primary particle size of 40 nm), 23% by weight of quartz glass powder (average particle size: 0.5 µm) and 30% by weight of barium glass powder (average particle size: 0.5 µm).

EP 3 363 423 B1 relates to dental milling blanks having the characteristic features of low water sorption, a high elastic modulus and high mechanical strength.

EP 3 685 798 B1 relates to dental milling blanks having the characteristic feature of low swelling, making them ideal for the production of retention-proof crowns and bridges.

What all these applications have in common is that the composite blocks are produced from pastes that would themselves be suitable also as direct filling materials and that also have the same advantages and disadvantages of composite-based filling materials.

EP 3 287 118 A1 describes a production process for dental milling blanks in which inorganic fillers, monomer matrix, initiators and colorants are intensively milled together with milling additives and milled material and then dried and finally compressed. The disadvantage of this process is the use of grinding beads in the presence of the initiators in the monomer matrix. The locally high energy input can lead locally to the occurrence of small premature polymerization zones that then constitute inhomogeneities in the finished product.

EP 2 881 077 A1 is directed to milling blanks that should have excellent mechanical properties, excellent abrasion resistance and excellent surface gloss. These properties should be achieved here via process technology. In contrast to the conventional production methods in which the composite material is processed by homogeneous mixing and kneading of a curable monomer mixture with a filler into a paste that needs to have a certain flowability in order to be cured to a milling blank in a mold, this application proposes hot-pressing the inorganic filler so as to aggregate it and then finally infiltrating it with the curable resin. The resin should thus fill the interstitial spaces in the primary particles and can then be cured. This process should allow the production of blanks in which the filler particles lie closer to one another than is possible in the conventional production process and thus make it possible to provide milling blanks having a particularly high filler content.

An analogous process is also described in applications JP 2017-109036 A, JP 2019-098073 A and JP 2019-098074 A from the same applicant.

The disadvantage of this process is that the filler has already been very highly compacted prior to the resin infiltration and that the resin infiltration occurs only from the surface. There is therefore the risk that the resin does not completely reach and fill all the interstitial spaces, especially in the center of the milling blank.

The objective of the present invention was thus to provide a process with which it is possible to produce dental milling blanks that not only are highly compacted but reliably exhibit the homogeneous resin-filler distribution of conventional dental milling blanks produced from pastes.

This objective is achieved by a process for producing a dental milling blank comprising the following steps:
i) producing or providing an inorganic filler powder (F)
ii) at least partial coating of the surface of the inorganic filler powder (F) by reaction with a silane (S) of formula

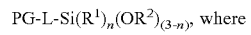

PG-L-Si(R$^1$)$_n$(OR$^2$)$_{(3-n)}$, where

PG is a polymerizable group,
L is a linker group that links the polymerizable group PG to the silicon atom
R$^1$ is a C1 to C4 alkyl group or phenyl group,
R$^2$ is a C1 to C4 alkyl group or a hydrogen atom,
n=0, 1 or 2,
wherein a surface-coated powder (F$_{sil}$) is obtained,
iii) adsorbing on the surface of the filler powder obtained in step ii (F$_{sil}$) of a liquid polymerizable composition (M), capable of polymerizing with the polymerizable group PG, wherein a surface-adsorbed powder (F$_{sil,ads}$) is obtained,
iv) filling of the powder obtained in step iii (F$_{sil,ads}$) into a mold,
v) compressing of the powder (F$_{sil,ads}$) in the mold under pressure and
vi) polymerizing of the polymerizable composition M and of the polymerizable groups PG.

Preferably, the adsorbing of the liquid polymerizable composition (M) in step iii is effected by low-energy mixing, preferably in a shaker-mixer or a rotary mixer.

Preferably, the adsorbing of the liquid polymerizable composition (M) in step iii is effected without an (energy-intensive) milling process, preferably without addition of a milling additive and/or milling medium. In particular, it is preferable that no volatile organic solvents as milling additive and/or no agate or zirconium dioxide beads as milling medium are added.

A preferred embodiment constitutes a corresponding process wherein the process additionally comprises one or more of the following steps:
vii) demolding of the milling blank obtained in step vi and/or
viii) further processing of the milling blank obtained in step vi and/or
ix) securing of a pin on the surface of the milling blank so as to secure the milling blank in a milling machine.

It was surprisingly found that the process according to the invention affords in steps i to iii a powder in which the polymerizable composition is adsorbed on the surface, but which can be handled and processed like a powder. In particular, the flowability of the powder allows it to be readily filled into molds (step iv). Thus, it is possible for example for differently colored powders to be successively filled into a mold. It is also possible for example for two (or more) differently colored powders to be concomitantly filled, with mixing, into a mold while varying the mixing ratio during the filling process, preferably continuously. These two processes make it possible to obtain multicolored dental milling blanks that are either made up of differently colored layers or have a continuous color gradient. Such dental milling blanks are ideal for recreating the natural color gradation of teeth.

At the same time, compaction of the surface-adsorbed powders make it possible to produce dental milling blanks that have very good mechanical properties, in particular high strength, a high elastic modulus and high abrasion stability. This is achieved not just by the homogeneous resin/filler distribution achieved by the adsorption process but also through minimization of defects arising from compaction.

In an advantageous configuration of a process according to the invention, the compression in step v, which is preferably uniaxial or biaxial, is carried out at a pressure in the range from 400 to 12000 bar, preferably in the range from 2500 to 10 000 bar, more preferably in the range from 4000 to 10 000 bar.

In an advantageous configuration of a process according to the invention, the polymerization in step vi, which is preferably isostatic, is carried out at a pressure in the range from 50 to 750 bar, preferably in the range from 100 to 600 bar, more preferably in the range from 200 to 500 bar, and/or (preferably and) at a temperature in the range from 60 to 160° C., preferably in the range from 80 to 140° C.

In another advantageous configuration of a process according to the invention, the compacting step v and the polymerizing step vi are carried out concomitantly at a temperature in the range from 60 to 160° C., preferably in the range from 80 to 140° C., through uniaxial or biaxial pressure in the range from 400 to 12000 bar, preferably in the range from 2500 to 10 000 bar, more preferably in the range from 4000 to 10 000 bar, or isostatic pressure in the range from 50 to 750 bar, preferably in the range from 100 to 600 bar, more preferably in the range from 200 to 500 bar.

In an advantageous configuration, the inorganic filler powder (F) produced or provided in step i comprises one or more inorganic fillers selected from the group consisting of barium silicate glasses, barium aluminosilicate glasses, barium borosilicate silicate glasses, barium boroaluminosilicate glasses, barium fluoroboroaluminosilicate glasses, strontium silicate glasses, strontium aluminosilicate glasses, strontium borosilicate glasses, strontium boroaluminosilicate silicate glasses, strontium fluoroboroaluminosilicate glasses, zirconium silicate glasses, quartz, cristobalite, fumed silica and ytterbium fluoride, preferably selected from the group consisting of barium boroaluminosilicate silicate glasses, fumed silica and ytterbium fluoride.

In an advantageous configuration, the inorganic filler powder F has a D50 value of from 0.18 to 10 µm, preferably from 0.4 to 5 µm.

In an advantageous configuration, the inorganic filler powder F comprises a first inorganic filler powder F1 and a second inorganic filler powder F2. The first inorganic filler powder F1 and the second inorganic filler powder F2 may differ here both in their chemical composition and in their particle size.

In another advantageous configuration, the first inorganic filler powder F1 has a D50 value of from 0.4 to 1.0 µm, preferably from 0.5 to 0.9 µm, and the second inorganic filler powder F2 has a D50 value of from 1.2 to 5.0 µm, preferably from 1.5 to 4.0 µm.

"At least partial coating" in step ii is understood as meaning that the inorganic filler powder (F) comprises constituents that, due to the presence of free Si—OH groups, are capable of reacting with the silane PG-L-Si($R^1$)$_n$ ($OR^2$)$_{(3-n)}$. The inorganic filler powder (F) may additionally also comprise further constituents that have no free Si—OH groups and are accordingly unable to react with the silane PG-L-Si($R^1$)$_n$($OR^2$)$_{(3-n)}$. Examples thereof are ytterbium fluoride, which does not contain any Si—OH groups, or hydrophobized silica in which the Si—OH groups have already undergone other reactions. Preferably, the inorganic filler powder (F) contains at least 50% by weight, preferably at least 70% by weight, particularly preferably at least 90% by weight and very particularly preferably 100% by weight, of constituents capable of reacting with the silane PG-L-Si ($R^1$)$_n$($OR^2$)$_{(3-n)}$.

The silane PG-L-Si($R^1$)$_n$($OR^2$)$_{(3-n)}$ used in step ii has a polymerizable group PG capable of (co)polymerizing with the polymerizable composition (M) adsorbed in step iii. Preferably, PG is a (meth)acryl or (meth)acrylamide group. "(Meth)acryl" is understood here as meaning both "methacryl" and "acryl".

In a preferred embodiment, the polymerizable group PG of the silane PG-L-Si($R^1$)$_n$($OR^2$)$_{(3-n)}$ is selected from the group consisting of —OC(=O)CH=$CH_2$, —OC(=O)C ($CH_3$)=$CH_2$, —NHC(=O)CH=$CH_2$ and —NHC(=O)C ($CH_3$)=$CH_2$, preferably —OC(=O)CH=$CH_2$ and —OC (=O)C($CH_3$)=$CH_2$, more preferably —OC(=O)C($CH_3$) =$CH_2$.

In a preferred embodiment, the linker group L of the silane PG-L-Si($R^1$)$_n$($OR^2$)$_{(3-n)}$ is an alkylene group having 1 to 12 carbon atoms, which may be interrupted by an oxygen atom or a urethane group.

Preferably, L is selected from the group consisting of —($CH_2$)$_p$—, —($CH_2$)$_q$—OC(=O)NH—($CH_2$)$_p$— and —($CH_2$)$_q$—NHC(=O)O—($CH_2$)$_p$—, where p=1 to 8 and q=2 to 4.

In a preferred embodiment, the silane PG-L-Si($R^1$)$_n$ ($OR^2$)$_{(3-n)}$ is a silane selected from the group consisting of $H_2C$=C($CH_3$)C(=O)O—($CH_2$)$_p$—Si($OR^2$)$_3$, $H_2C$=C ($CH_3$)C(=O)O—($CH_2$)$_q$—NHC(=O)O—($CH_2$)$_p$—Si ($OR^2$)$_3$ and $H_2C$=C($CH_3$)C(=O)O—($CH_2$)$_q$—OC(=O) NH—($CH_2$)$_p$—Si($OR^2$)$_3$, where $R^2$ is a C1 to C4 alkyl group where p=1 to 8 and q=2 to 4.

In a particularly preferred embodiment, the silane PG-L-Si($R^1$)$_n$($OR^2$)$_{(3-n)}$ is a silane selected from the group consisting of
$H_2C$=C($CH_3$)C(=O)O—($CH_2$)—Si($OR^2$)$_3$, $H_2C$=C ($CH_3$)C(=O)O—($CH_2$)$_3$—Si($OR^2$)$_3$, $H_2C$=C($CH_3$)C (=O)O—($CH_2$)$_2$—NHC(=O)O—($CH_2$)$_3$—Si($OR^2$)$_3$ and $H_2C$=C($CH_3$)C(=O)O—($CH_2$)$_2$—OC(=O)NH—($CH_2$)$_3$ —Si($OR^2$)$_3$, where $R^2$ is a C1 to C4 alkyl group.

Very particularly preferably, the silane is 3-methacryloyloxypropyltrimethoxysilane.

In a preferred embodiment, the liquid polymerizable composition (M) comprises

A) one, two or more polymerizable monomers, preferably (meth)acrylates and/or (meth)acrylamides, B) an initiator or an initiator system, C) optionally inorganic, non-agglomerated, non-aggregated particles having an average particle size of less than 80 nm and D) optionally colorants.

"(Meth)acryl" is understood here as meaning both "methacryl" and "acryl".

The polymerizable monomer (A) preferably consists of (meth)acrylates.

The polymerizable monomer (A) preferably comprises one or more monomers selected from ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, neopentyl glycol di(meth)acrylate, butane-1,4-diol di(meth) acrylate, hexane-1,6-diol di(meth)acrylate, nonane-1,9-diol di(meth)acrylate, decane-1,10-diol di(meth)acrylate, dodecane-1,12-diol di(meth)acrylate, tricyclo[5.2.1.0$^{2,6}$]decane- 3(4),8(9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5,12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl)carbamoylmethyl]-3-(2-(meth)acryloyloxyethyl)carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl-9'-ene)phenyl, 1,3-bis(1',1',9'-trimethyl-3',8'-dioxo-2'-aza-4',7'-dioxa-decyl-9'-ene)phenyl, 3(4),8(9)-bis(4',7'-dioxa-3',8'-dioxo-2'-aza-decyl-9'-ene)tetrahydrodicyclopentadiene, 3(4),8(9)-bis(4',7'-dioxa-3',8'-dioxo-2'-aza-9'-methyl-decyl-9'-ene)tetrahydrodicyclopentadiene, trimethylolpropane di(meth)acrylate, trimethylolpropane tri(meth)acrylate, ethoxylated trimethylolpropane tri(meth)acrylate, ditrimethylolpropane tetra(meth)acrylate, ethoxylated ditrimethylolpropane tetra(meth)acrylate, pentaerythritol di(meth)acrylate, pentaerythritol tri(meth)acrylate, pentaerythritol tetra(meth)acrylate, dipentaerythritol tetra(meth)acrylate, dipentaerythritol penta(meth)acrylate, dipentaerythritol hexa(meth)acrylate, 2,2-bis[4-[3-(meth)acryloyloxy-2-hydroxypropoxy]phenyl]propane, 2,2-bis[4-[2-(meth)acryloyloxy-3-hydroxypropoxy]phenyl]propane, ethoxylated bisphenol A di(meth)acrylate, propoxylated bisphenol A di(meth)acrylate, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane, 2-[4-(meth)acryloyloxdipropoxyphenyl]-2-[4-(meth)acryloyloxytriethoxyphenyl]propane, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, methyl (meth)acrylate, ethyl (meth)acrylate, propyl (meth)acrylate, butyl (meth)acrylate, hexyl (meth)acrylate, 2-ethylhexyl (meth)acrylate, tetrahydrofurfuryl (meth)acrylate, isobornyl (meth)acrylate, lauryl (meth)acrylate, cyclohexyl (meth)acrylate, (octahydro-4,7-methano-1H-indenyl)methyl (meth)acrylate, benzyl (meth)acrylate and phenoxyethyl (meth)acrylate, preferably selected from the group consisting of triethylene glycol di(meth)acrylate, tetraethylene glycol di(meth)acrylate, hexane-1,6-diol di(meth)acrylate, decane-1,10-diol di(meth)acrylate, dodecane-1,12-diol di(meth)acrylate, tricyclo[5.2.1.0$^{2,6}$]decane-3(4),8(9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5,12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl)carbamoylmethyl]-3-(2-(meth)acryloyloxyethyl)carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl-9'-ene)phenyl, 1,3-bis(1',1',9'-trimethyl-3',8'-dioxo-2'-aza-4',7'-dioxa-decyl-9'-ene)phenyl, 3(4),8(9)-bis(4',7'-dioxa-3',8'-dioxo-2'-aza-decyl-9'-ene)tetrahydrodicyclopentadiene, 3(4),8(9)-bis(4',7'-dioxa-3',8'-dioxo-2'-aza-9'-methyl-decyl-9'-ene)tetrahydrodicyclopentadiene, 2,2-bis[4-[3-(meth)acryloyloxy-2-hydroxypropoxy]phenyl]propane, 2,2-bis[4-[2-(meth)acryloyloxy-3-hydroxypropoxy]phenyl]propane, ethoxylated bisphenol A di(meth)acrylate, propoxylated bisphenol A di(meth)acrylate, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane and 2-[4-(meth)acryloyloxdipropoxyphenyl]-2-[4-(meth)acryloyloxytriethoxyphenyl]propane.

The proportion of polymerizable monomers (A) is 39% to 99% by weight, preferably 39% to 79% by weight, more preferably 39% to 59% by weight, based on the total mass of the liquid polymerizable composition (M).

In a preferred embodiment, the initiator or initiator system (B) is a thermal initiator. Suitable thermal initiators are ketone peroxides, peroxyketals, hydroperoxides, dialkyl peroxides, diacyl peroxides, peroxyesters, peroxydicarbonates and azo compounds. Preferably, (B) is selected from the group consisting of dibenzoyl peroxide, bis(2,4-dichlorobenzoyl) peroxide, dilauroyl peroxide, dicumyl peroxide, tert-butyl perbenzoate, cumene hydroperoxide, tert-butyl peroxy-3,5,5-trimethylhexanoate, 2,2'-azobisisobutyronitrile, 2,2'-azobis(2-methylbutyronitrile), 2,2'-azobis-2,4-dimethylvaleronitrile, 2,2'-azobis-1-cyclohexanecarbonitrile and dimethyl 2-2'-azobisisobutyrate. More preferably, (B) is selected from the group consisting of dibenzoyl peroxide, bis(2,4-dichlorobenzoyl) peroxide, dilauroyl peroxide and 2,2'-azobisisobutyronitrile.

Particularly preferably, (B) is dibenzoyl peroxide.

The proportion of initiators (B) is 0.5% to 5% by weight, preferably 0.5% to 3.0% by weight, more preferably 1.0% to 2.5% by weight, based on the total mass of the liquid polymerizable composition (M).

The liquid polymerizable composition (M) is preferably free of non-polymerizable solvents, preferably free of solvents.

In a preferred embodiment, the liquid polymerizable composition (M) comprises inorganic, non-agglomerated, non-aggregated particles (C). These particles have an average particle size of less than 80 nm. Average particle size is here understood as meaning the volume-weighted D50 value, which can be determined by DLS measurement. The inorganic, non-agglomerated, non-aggregated particles (C) preferably have a D50 value of from 8 to 80 nm, preferably from 10 to 60 nm.

It is advantageous when the nanoparticles are present in a monodisperse and completely dispersed form.

The proportion of inorganic, non-agglomerated, non-aggregated particles (C) is 0% to 60% by weight, preferably 20% to 60% by weight, more preferably 40% to 60% by weight, based on the total mass of the liquid polymerizable composition (M).

In a preferred embodiment, the inorganic, non-agglomerated, non-aggregated particles (C) are nanoscale silica. Such silicas can be produced for example by sol-gel processes and are commercially available for example under the "Nalco Colloidal Silicas" (Nalco Chemical Co.), "Ludox colloidal silica" (Grace) or "Highlink OG" (Clariant) names.

To ensure good incorporation of the nanoparticles into the polymer matrix, the nanoscale silica particles are preferably surface-coated with a silane. Preference is given to using a silane of formula PG-L-Si($R^1$)$_n$(O$R^2$)$_{(3-n)}$, where PG, L, $R^1$, $R^2$ and n are as already defined further above in connection with the inorganic filler powder (F) and the silane (S). For the silane used for surface-coating the nanoscale silica particles, the same preferred configurations apply as already described above for the silane (S). The surface-coating of the inorganic filler powder (F) and of the inorganic, non-agglomerated, non-aggregated silica-based particles (C) can be carried out using the same silane or using two different silanes which in each case correspond to the formula PG-L-Si($R^1$)$_n$(O$R^2$)$_{(3-n)}$. Particular preference is however here also given to using 3-methacryloyloxypropyltrimethoxysilane.

In another preferred embodiment, the inorganic, non-agglomerated, non-aggregated particles (C) are nanoscale ytterbium fluoride (YbF$_3$).

To ensure good incorporation of the nanoparticles into the polymer matrix, the nanoscale ytterbium fluoride are preferably surface-coated with 10-[(2-methylprop-2-enoyl)oxy]decyl dihydrogen phosphate (MDP).

In a preferred embodiment, the liquid polymerizable composition (M) contains 40% to 60% by weight of non-agglomerated, non-aggregated SiO$_2$ and/or YbF$_3$ particles having a D50 value of 10 to 60 nm.

In order to permit the most true-to-life, tooth-like restoration possible, a milling blank produced according to the invention comprises colorants.

The colorants are inorganic color pigments, organic color pigments or dyes. For a tooth-like appearance, white, yellow, orange, red, brown and black colorants are used.

The colorants are preferably inorganic color pigments selected from the group consisting of iron oxide, titanium dioxide, barium sulfate and aluminum oxide.

Depending on the chemical nature of the colorants and on the particle size thereof in the case of color pigments, the colorants may be added in different steps of the process according to the invention.

Soluble organic dyes are advantageously dissolved in the liquid polymerizable composition (M) and added therewith in step iii.

Inorganic or organic color pigments with a small particle size, especially with a particle size of less than 80 nm, can also likewise be readily dispersed in the liquid polymerizable composition (M) and added therewith in step iii.

It is however also possible for inorganic or organic color pigments to be added at an earlier stage, to the inorganic filler powder (F) in step i and mixed in therewith.

In addition, it is also possible for inorganic or organic color pigments to be added either in the silanization step ii or in the adsorption step iii.

The invention therefore encompasses a process for producing a dental milling blank wherein one or more colorants are added in one of steps i, ii or iii or wherein the liquid polymerizable composition (M) comprises colorants (D).

The invention also encompasses a process a process for producing a dental milling blank in which steps i to iv are repeated one layer at a time and the powder layers compressed together in step v or in which steps i to v are repeated one layer at a time, wherein each of the individual layers is differently colored by means of different colorants and/or by means of different amounts of colorant.

The invention also encompasses a process for producing a dental milling blank in which two (or more) differently colored surface-adsorbed powders $F_{sil,ads,1}$ and $F_{sil,ads,2}$ (and further $F_{sil,ads,x}$ if present) are each produced in parallel in steps i to iii and are in step vi filled, with mixing, into a mold, wherein the mixing ratio of $F_{sil,ads,1}$ to $F_{sil,ads,2}$ (and to further $F_{sil,ads,x}$, if present) is altered during filling, preferably continuously altered.

The invention also encompasses a process for producing a dental milling blank that includes between steps v and vi a step v-a in which the compressed shaped article is immersed in a colorant solution.

Preferably, the colorant solution comprises colorants and polymerizable monomers and optionally initiators. The colorants are preferably the colorants already described as colorants (D). The polymerizable monomers are preferably the monomers already described as monomers (A). The initiators are preferably the initiators already described as initiators (B).

In a preferred embodiment, the liquid polymerizable composition (M) comprises
 A) in an amount of from 39% to 99% by weight, preferably 39% to 79% by weight, more preferably 39% to 59% by weight,
 B) in an amount of from 0.5% to 5% by weight, preferably 0.5% to 3.0% by weight, more preferably 1.0% to 2.5% by weight,
 C) in an amount of from 0% to 60% by weight, preferably 20% to 60% by weight, more preferably 40% to 60% by weight and
 D) in an amount of from 0% to 1% by weight, preferably 0% to 0.5% by weight, more preferably 0.0001% to 0.1% by weight,
in each case based on the total mass of the liquid polymerizable composition (M).

The process according to the invention makes it possible to produce dental milling blanks having a particularly high filler content.

In a preferred embodiment, the mass ratio of surface-coated powder ($F_{sil}$) to liquid polymerizable composition (M) is in the range from 3:1 to 10:1, preferably in the range from 4:1 to 9:1 and more preferably in the range from 5:1 to 8:1.

In a preferred embodiment, the total filler content, i.e. the sum total of the mass fractions of the surface-coated powder ($F_{sil}$) and of the inorganic, non-agglomerated, non-aggregated particles (C), if present, is in the range from 80% by weight to 95% by weight, preferably in the range from 83% by weight to 94% by weight and more preferably in the range from 85% by weight to 93% by weight, in each case based on the total mass of the milling blank.

The invention also encompasses a dental milling blank produced by a process according to the invention, especially a dental milling blank produced by compressing and polymerizing an inorganic filler powder ($F_{sil,ads}$), on the surface of which is present
 a coating with a silane (S) PG-L-Si($R^1$)$_n$(O$R^2$)$_{(3-n)}$, where PG is a polymerizable group, L is a linker group that links the polymerizable group PG to the silicon atom, $R^1$ is a C1 to C4 alkyl group or phenyl group, $R^2$ is a C1 to C4 alkyl group or a hydrogen atom and n=0, 1 or 2,
 and
  a liquid polymerizable composition (M) adsorbed thereon, comprising
   (A) one, two or more polymerizable monomers, preferably (meth)acrylates and/or (meth)acrylamides,
   (B) an initiator or an initiator system, preferably a thermal initiator, (C) optionally inorganic, non-agglomerated, non-aggregated particles having an average particle size of less than 80 nm and (D) optionally colorants.

The advantageous configurations described further above for the production process in relation to the individual constituents (inorganic powder F, silane S, polymerizable group PG, linker group L, $R^1$, $R^2$, n, p, q, polymerizable composition M, polymerizable monomers A, initiators B, nanofillers C, colorants D) are considered preferred for the milling blank too. Preferred features are preferably combined with one another.

It is advantageous when the milling blanks according to the invention or milling blanks produced by the process of the invention are assembled in the form of kits.

The invention also encompasses a kit comprising a plurality of milling blanks produced by the process of the invention, wherein the milling blanks have the same monochrome color or have different monochrome colors or have the same layered color gradation or have the same continuous color gradation.

The invention also encompasses a kit comprising one or more milling blanks produced by the process of the invention, a conditioning agent for indirect restorations produced from the milling blanks and a luting material for luting indirect restorations produced from the milling blanks.

The invention will now be elucidated in more detail hereinbelow with reference to examples:

Abbreviations (Substances Used)

F1: Barium aluminum borosilicate glass (D50 0.8 µm/D25 0.5 µm/D75 1.0 µm)

F2: Barium aluminum borosilicate glass (D50 2.7 µm/D25 1.4 µm/D75 6.1 µm)

F3: Barium aluminum borosilicate glass (D50 0.18 µm; GM27884 NF180, Schott)

Bis-GMA: 2,2-Bis[4-methacryloyloxypolyethoxyphenyl] propane (CAS 1565-94-2)

Bis-EMA2.6: Ethoxylated bisphenol A dimethacrylate containing an average of 2.6 ethylene oxide units (CAS 41637-38-1)

UDMA: 7,7,9(7,9,9)-Trimethyl-4,13-dioxo-3,14-dioxa-5,12-diazahexadecane-1,16-diyl dimethacrylate (CAS 72869-86-4)

TCDDMA: Bis(methacryloyloxymethyl)tricyclo [5.2.1.0$^{2,6}$]decane (CAS 43048-08-4)

TEGDMA: Triethylene glycol dimethacrylate (CAS 109-16-0)

HDDMA: 1,6-Hexanediol dimethacrylate (CAS 6606-59-3)

MPS: 3-Methacryloyloxypropyltrimethoxysilane (CAS 2530-85-0)

MOS: 8-Methacryloyloxyoctyltrimethoxysilane (CAS 122749-49-9)

BPO: Dibenzoyl peroxide (CAS 94-36-0)

TPO: 2,4,6-Trimethylbenzoyldiphenylphosphine oxide (CAS 75980-60-8)

BHT: 2,6-Di-tert-butyl-4-methylphenol (CAS 128-37-0

DEPT: N,N-Dihydroxyethyl-4-methylaniline (CAS 3077-12-1)

3-Point flexural strength (3PFS): The flexural strength was determined in accordance with DIN EN ISO 6872:2009 (7.3.2) with a span width of 12 mm and a support roller diameter of 2 mm. For this, test specimens with a width of 4 mm, a thickness of 1.2 mm and a length of 15 mm were produced from the composite blocks using a high-speed saw (IsoMet 4000, Buehler) and deburred, ground and polished. The specimens were loaded with a crosshead speed of 1 mm/min until fracture and the 3-point flexural strength calculated according to the formula given in 7.3.2.4.1.

Elastic modulus (E): The elastic modulus was determined in accordance with the calculation in ADA spec. No. 27:1993 (7.8.4.2) as the slope of the stress-strain curve of the 3-point flexural strength determination in the linear-elastic region.

$$E = \frac{3}{4} \frac{L}{b h^3} \frac{\Delta F}{\Delta d}$$

(L: span width; b: sample width; h: sample thickness; $\Delta d$: deformation in the linear-elastic region; $\Delta F$: force change at deformation $\Delta d$)

Ignition residue (IR): For the determination of the ignition residue, a composite block was in each case milled and the milling residue then homogenized. About 0.5 g of the milling residue was heated at 575° C. in a porcelain crucible for 2 hours. The ignition residue is given by $$G = \frac{m_{Auswaage}}{m_{Einwaage}} \times 100\%$$

($m_{initial\ weight}$: mass of the weighed, milled blocks before heating;

($m_{end\ weight}$: mass of the milled blocks after heating;

EXAMPLE 1A (FILLER F1$_{SIL}$-1A)

100.0 g of filler F1 is dispersed in 250 ml of ethanol. 4.0 g of MPS and 2.5 g of water are added and the mixture is stirred at room temperature for two hours. The solvent is then removed under reduced pressure and the mixture dried at 90° C. for three hours.

EXAMPLE 1B (FILLER F2$_{SIL}$-1B)

100.0 g of filler F2 is dispersed in 250 ml of ethanol. 4.0 g of MPS and 2.5 g of water are added and the mixture is stirred at room temperature for two hours. The solvent is then removed under reduced pressure and the mixture dried at 90° C. for three hours.

EXAMPLE 1C (FILLER F3$_{SIL}$-1C)

100.0 g of filler F3 (GM27884, NF180) is dispersed in 250 ml of ethanol. 4.0 g of MPS and 2.5 g of water are added and the mixture is stirred at room temperature for two hours. The solvent is then removed under reduced pressure and the mixture dried at 90° C. for three hours.

EXAMPLE 1D (FILLER F1$_{SIL}$-1D)

100.0 g of filler F1 is dispersed in 250 ml of ethanol. 4.0 g of MOS and 2.5 g of water are added and the mixture is stirred at room temperature for two hours. The solvent is then removed under reduced pressure and the mixture dried at 90° C. for three hours.

EXAMPLE 1E (FILLER F2$_{SIL}$-1E)

100.0 g of filler F2 is dispersed in 250 ml of ethanol. 4.0 g of MOS and 2.5 g of water are added and the mixture is stirred at room temperature for two hours. The solvent is then removed under reduced pressure and the mixture dried at 90° C. for three hours.

EXAMPLE 2A (RESIN 2A)

500.0 g of Organosilicasol MIBK-SD-L (30%, 40 nm), 60.0 g of bis-EMA2.6, 37.5 g of UDMA and 37.5 g of TCDDMA are stirred at room temperature for one hour until a homogeneous solution has formed. The solvent is then removed under reduced pressure. 3.0 g of BPO is then added and the mixture stirred at room temperature for a further two hours until the BPO has dissolved completely.

EXAMPLE 2B (RESIN 2B)

100.0 g of UDMA, 25.0 g of TEGDMA, 0.25 g of BPO, 0.30 g of BHT and 0.325 g of DEPT are stirred at room temperature for two hours until the solids have dissolved completely.

EXAMPLE 2C (RESIN 2C)

50.0 g of bis-GMA, 50.0 g of HDDMA, 0.5 g of TPO and 1.0 g of BPO are stirred at room temperature for two hours until the solids have dissolved completely.

EXAMPLE 3A (FILLER F$_{SIL,ADS}$-3A)

To 70.5 g of filler F2$_{sil}$-1b is added 29.5 g of resin 2a in four portions and the mixture is mixed at 72 rpm for 16 hours at room temperature in a Turbula T2F shaker-mixer (Willy A. Bachofen GmbH, Germany).

EXAMPLE 3B (FILLER F$_{SIL,ADS}$-3B)

To 76.0 g of filler F2$_{sil}$-1b is added 24.0 g of resin 2a in four portions and the mixture is mixed at 72 rpm for 16 hours at room temperature in a Turbula T2F shaker-mixer.

EXAMPLE 3C (FILLER F$_{SIL,ADS}$-3C)

To 13.0 g of filler F1$_{sil}$-1a and 57.5 g of filler F2$_{sil}$-1b is added 29.5 g of resin 2a in four portions and the mixture is mixed at 72 rpm for 16 hours at room temperature in a Turbula T2F shaker-mixer.

EXAMPLE 3D (FILLER F$_{SIL,ADS}$-3D)

To 14.0 g of filler F1$_{sil}$-1a and 62.0 g of filler F2$_{sil}$-1b is added 24.0 g of resin 2a in four portions and the mixture is mixed at 72 rpm for 16 hours at room temperature in a Turbula T2F shaker-mixer.

EXAMPLE 3E (FILLER F$_{SIL,ADS}$-3E)

To 13.0 g of filler F1$_{sil}$-1d and 57.5 g of filler F2$_{sil}$-1e is added 29.5 g of resin 2a in four portions and the mixture is mixed at 72 rpm for 16 hours at room temperature in a Turbula T2F shaker-mixer.

EXAMPLE 3F (FILLER F$_{SIL,ADS}$-3F)

To 14.0 g of filler F1$_{sil}$-1d and 62.0 g of filler F2$_{sil}$-1e is added 24.0 g of resin 2a in four portions and the mixture is mixed at 72 rpm for 16 hours at room temperature in a Turbula T2F shaker-mixer.

EXAMPLE 3G (FILLER F$_{SIL,ADS}$-3G)

To 75.0 g of filler F2$_{sil}$-1b is added 25.0 g of resin 2b in four portions and the mixture is mixed at 72 rpm for 16 hours at room temperature in a Turbula T2F shaker-mixer.

EXAMPLE 4A 11.0 g of filler F$_{sil,ads}$-3a is filled into a steel mold (D 16 mm). Uniaxial pressure of 9750 bar is then applied in a laboratory press (MP250, Maassen GmbH, Germany) for 5 minutes. The blank is carefully removed from the mold and polymerized isostatically at 250 bar and the following temperature program (20° C.-2° C./min-120° C. (30 min)-5° C./min-20° C.).

EXAMPLES 4B TO 4G

Composite blocks are produced from powders F$_{sil,ads}$-3b to F$_{sil,ads}$-3g in analogous manner to example 4a.

EXAMPLE 4H 11.0 g of filler F$_{sil,ads}$-3c is filled into a steel mold (D 16 mm). Uniaxial pressure of 4875 bar is then applied in a laboratory press (MP250, Maassen GmbH, Germany) for 5 minutes. The blank is carefully removed from the mold and polymerized isostatically at 250 bar and the following temperature program (20° C.-2° C./min-120° C. (30 min)-5° C./min-20° C.).

TABLE 1

| | (example 4) | | | |
|---|---|---|---|---|
| Example | 4a | 4b | 4c | 4d |
| F1$_{sil}$-1a | — | — | 13.0 | 14.0 |
| F2$_{sil}$-1b | 70.5 | 76.0 | 57.5 | 62.0 |
| Resin 2a | 29.5 | 24.0 | 29.6 | 24.0 |
| Flexural strength | 269 | 281 | 291 | 295 |
| Elastic modulus | 13.8 | 14.2 | 18.5 | 19.1 |
| Appearance | homogeneous | homogeneous | homogeneous | homogeneous |
| Example | 4e | 4f | 4g | 4h |
| F1$_{sil}$-1a | 13.0 | 14.0 | — | 13.0 |
| F2$_{sil}$-1b | 57.5 | 62.0 | 75.0 | 57.5 |
| Resin 2a | 29.6 | 24.0 | 25.0 | 29.6 |
| Flexural strength | 283 | 289 | 258 | 290 |
| Elastic modulus | 18.5 | 19.1 | 14.3 | 18.4 |
| Appearance | homogeneous | homogeneous | homogeneous | homogeneous |

COMPARATIVE EXAMPLE 5A 70.5 g of filler F2$_{sil}$-1b and 29.5 g of resin 2a are kneaded at 50 rpm in a laboratory kneader (PC Laborsystem, Magden OH) for 30 minutes, this being accompanied after approx. 10 minutes by a change in the paste from pulverulent to pasty. The mixture in the laboratory kneader is then degassed at 50 rpm and −0.85 bar for a further 15 minutes. For production of the composite blocks, the paste is filled into molds (D 16 mm; h 20 mm). Polymerization is then carried out isostatically at 250 bar and the following temperature program (20° C.-2° C./min-120° C. (30 min)-5° C./min-20° C.).

COMPARATIVE EXAMPLE 5B 76.0 g of filler $F2_{sil}$-1b and 24.0 g of resin 2a are kneaded at 50 rpm in a laboratory kneader (PC Laborsystem, Magden CH) for 30 minutes. With this powder/liquid ratio, a change in the paste from pulverulent to pasty no longer occurs. Further processing of the composite paste into a composite block is therefore not possible.

COMPARATIVE EXAMPLE 5C 13.0 g of filler $F1_{sil}$-1a, 57.5 g of filler $F2_{sil}$-1b and 29.5 g of resin 2a are kneaded at 50 rpm in a laboratory kneader (PC Laborsystem, Magden CH) for 30 minutes, this being accompanied after approx. 10 minutes by a change in the paste from pulverulent to pasty. The mixture in the laboratory kneader is then degassed at 50 rpm and −0.85 bar for a further 15 minutes. For production of the composite blocks, the paste is filled into molds (D 16 mm; h 20 mm). Polymerization is then carried out isostatically at 250 bar and the following temperature program (20° C.-2° C./min-120° C. (30 min)-5° C./min-20° C.).

COMPARATIVE EXAMPLE 5D 14.0 g of filler $F1_{sil}$-1a, 62.0 g of filler $F2_{sil}$-1b and 24.0 g of resin 2a are kneaded at 50 rpm in a laboratory kneader (PC Laborsystem, Magden CH) for 30 minutes. With this powder/liquid ratio, a change in the paste from pulverulent to pasty no longer occurs. Further processing of the composite paste into a composite block is therefore not possible.

TABLE 2

(comparative example 5)

| | Comparative example | | | |
|---|---|---|---|---|
| | 5a | 5b | 5c | 5d |
| $F1_{sil}$-1a | — | — | 13.0 | 14.0 |
| $F2_{sil}$-1b | 70.5 | 76.0 | 57.5 | 62.0 |
| Resin 2a | 29.5 | 24.0 | 29.6 | 24.0 |
| Flexural strength | 221 | n.d.* | 274 | n.d.* |
| Elastic modulus | 13.4 | n.d.* | 18.3 | n.d.* |
| Appearance | homogeneous | n.d.* | homogeneous | n.d.* |

*not determined, as it was not possible to produce a block.

COMPARATIVE EXAMPLE 6A (FILLER V6A)

70.5 g of filler F2, 29.5 g of resin 2a, 200.0 g of ethanol and 50.0 g of zirconia grinding beads (Luvobead YZB, 1.0-1.2 mm) are milled in an agitator mill for 60 minutes. This is followed by a preliminary drying for 3 hours at 50° C. and a main drying for a further 3 hours at 50° C.

COMPARATIVE EXAMPLE 6B (FILLER V6B)

76.0 g of filler F2, 24.0 g of resin 2a, 200.0 g of ethanol and 50.0 g of zirconia grinding beads (Luvobead YZB, 1.0-1.2 mm) are milled in an agitator mill for 60 minutes. This is followed by a preliminary drying for 3 hours at 50° C. and a main drying for a further 3 hours at 50° C.

COMPARATIVE EXAMPLE 6C (FILLER V6C)

70.5 g of filler $F2_{sil}$-1b, 29.5 g of resin 2a, 200.0 g of ethanol and 50.0 g of zirconia grinding beads (Luvobead YZB, 1.0-1.2 mm) are milled in an agitator mill for 60 minutes. This is followed by a preliminary drying for 3 hours at 50° C. and a main drying for a further 3 hours at 50° C.

COMPARATIVE EXAMPLE 6D (FILLER V6D)

76.0 g of filler $F2_{sil}$-1b, 24.0 g of resin 2a, 200.0 g of ethanol and 50.0 g of zirconia grinding beads (Luvobead YZB, 1.0-1.2 mm) are milled in an agitator mill for 60 minutes. This is followed by a preliminary drying for 3 hours at 50° C. and a main drying for a further 3 hours at 50° C.

COMPARATIVE EXAMPLE 6E (FILLER V6E)

75.0 g of filler F2, 25.0 g of resin 2b, 100.0 g of ethanol and 100.0 g of zirconia grinding beads (Luvobead YZB, 1.0-1.2 mm) are milled in an agitator mill for 90 minutes. This is followed by a preliminary drying for 3 hours at 40° C. and a main drying for a further 3.5 hours at 40° C.

COMPARATIVE EXAMPLE 7A 11.0 g of filler V6a is filled into a steel mold (D 16 mm). Uniaxial pressure of 10 MPa is then applied in a laboratory press (MP250, Maassen GmbH, Germany) for 5 minutes. The blank is carefully removed from the mold and polymerized isostatically at 130 MPa and 150° C. for 90 minutes.

COMPARATIVE EXAMPLE 7B TO 7E

Composite blocks are produced from powders V6b to V6e in analogous manner to comparative example 7a.

TABLE 3

(comparative example 7)

| | Comparative example | | | | |
|---|---|---|---|---|---|
| | 7a | 7b | 7c | 7d | 7e |
| F2 | 70.5 | 76.0 | — | — | 75.0 |
| $F2_{sil}$-1b | — | — | 70.5 | 76.0 | — |
| Resin 2a | 29.5 | 24.0 | 29.5 | 24.0 | — |
| Resin 2b | — | — | — | — | 25.0 |
| Flexural strength | 203 | 211 | 212 | 216 | 202 |
| Elastic modulus | 10.7 | 11.5 | 10.8 | 11.9 | 10.6 |
| Appearance | Inhomogeneous | Inhomogeneous | Inhomogeneous | Inhomogeneous | Inhomogeneous |

The test specimens in the flexure test were examined under a microscope at the points of fracture. The test specimens exhibited a large number of inhomogeneities that suggested that a partial premature polymerization had taken place during the milling process or during the drying process.

COMPARATIVE EXAMPLE 8A 11.0 g of filler V6a is filled into a steel mold (D 16 mm). Uniaxial pressure of 9750 bar is then applied in a laboratory press (MP250, Maassen GmbH, Germany) for 5 minutes. The blank is carefully removed from the mold and polymerized isostatically at 250 bar and the following temperature program (20° C.-2° C./min-120° C. (30 min)-5° C./min-20° C.).

COMPARATIVE EXAMPLES 8B TO 8E

Composite blocks are produced from powders V6b to V6e in analogous manner to comparative example 8a.

TABLE 4

(comparative example 8)

| | Comparative example | | | | |
|---|---|---|---|---|---|
| | 8a | 8b | 8c | 8d | 8e |
| F2 | 70.5 | 76.0 | — | — | 75.0 |
| F2$_{sil}$-1b | — | — | 70.5 | 76.0 | — |
| Resin 2a | 29.5 | 24.0 | 29.5 | 24.0 | — |
| Resin 2b | — | — | — | — | 25.0 |
| Flexural strength | 205 | 218 | 215 | 229 | 205 |
| Elastic modulus | 10.6 | 11.8 | 10.9 | 12.1 | 10.8 |
| Appearance | Inhomogeneous | Inhomogeneous | Inhomogeneous | Inhomogeneous | Inhomogeneous |

Here too, the test specimens exhibited a large number of inhomogeneities that suggested that a partial premature polymerization had taken place during the milling process or during the drying process.

COMPARATIVE EXAMPLE 9A 5.5 g of filler F2$_{sil}$-1b is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 10 ml of resin 2a and allowed to stand at room temperature with exclusion of light for 12 hours. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

COMPARATIVE EXAMPLE 9B 11.0 g of filler F2$_{sil}$-1b is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 20 ml of resin 2a and allowed to stand at room temperature with exclusion of light for 12 hours. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

COMPARATIVE EXAMPLE 9C 11.0 g of filler F2$_{sil}$-1b is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 20 ml of resin 2a and allowed to stand at room temperature with exclusion of light for 4 days. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

COMPARATIVE EXAMPLE 9D 5.5 g of filler F3$_{sil}$-1c is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 10 ml of resin 2c and allowed to stand at room temperature with exclusion of light for 12 hours. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

COMPARATIVE EXAMPLE 9E 11.0 g of filler F3$_{sil}$-1c is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 20 ml of resin 2c and allowed to stand at room temperature with exclusion of light for 12 hours. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

COMPARATIVE EXAMPLE 9F 11.0 g of filler F3$_{sil}$-1c is filled into a steel mold (D 16 mm). Uniaxial pressure of 68.6 MPa is then applied in a laboratory press (MP250, Maassen GmbH, Germany) for 3 minutes. The blank is carefully removed from the mold, immersed in 20 ml of resin 2c and allowed to stand at room temperature with exclusion of light for 4 days. The pressure is then reduced while keeping the blank immersed and the system is degassed (10 hPa, 10 minutes). The blank is carefully removed from the resin, laid on a glass plate and photopolymerized in a light box (Individo Light Box, VOCO GmbH, Deutschland) for 5 minutes. This is followed by a thermal polymerization at 130° C. for 20 minutes.

TABLE 5

(comparative example 9)

| | Comparative example | | | | | |
|---|---|---|---|---|---|---|
| | 9a | 9b | 9c | 9d | 9e | 9f |
| Filler | F2$_{sil}$-1b | | | F3$_{sil}$-1c | | |
| Harz | Resin 2a | | | Resin 2c | | |
| Ignition residue | 81.5% | 70.3% | 81.3% | 81.8% | 70.7% | 81.5% |
| Flexural strength | 170 | 150 | 168 | 173 | 151 | 169 |
| Elastic modulus | 12.4 | 9.9 | 12.3 | 12.8 | 10.1 | 12.7 |

An infiltration time long enough to achieve maximum possible saturation with the resin was found to be necessary, especially for blocks in clinically relevant dimensions. Nevertheless, it is from the outside possible to determine only with difficulty the degree of infiltration during the immersion period so as to avoid premature removal.

The invention can be summarized on the basis of the aspects that follow.

1. Process for producing a dental milling blank comprising the following steps:
   i) producing or providing an inorganic filler powder (F),
   ii) at least partial coating of the surface of the inorganic filler powder (F) by reaction with a silane (S) of formula

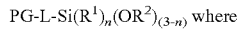
   $PG\text{-}L\text{-}Si(R^1)_n(OR^2)_{(3-n)}$ where

PG is a polymerizable group,
   L is a linker group that links the polymerizable group PG to the silicon atom
   $R^1$ is a C1 to C4 alkyl group or phenyl group,
   $R^2$ is a C1 to C4 alkyl group or a hydrogen atom,
   n=0, 1 or 2,
   wherein a surface-coated powder ($F_{sil}$) is obtained,
   iii) adsorbing on the surface of the filler powder obtained in step ii ($F_{sil}$) of a liquid polymerizable composition (M), capable of polymerizing with the polymerizable group PG, wherein a surface-adsorbed powder ($F_{sil,ads}$) is obtained,
   iv) filling of the powder obtained in step iii ($F_{sil,ads}$) into a mold,
   v) compressing of the powder ($F_{sil,ads}$) in the mold under pressure and
   vi) polymerizing of the polymerizable composition M and of the polymerizable groups PG.

2. Process for producing a dental milling blank according to aspect 1, wherein the process additionally comprises one or more of the following steps:
   vii) demolding of the milling blank obtained in step vi and/or
   viii) further processing of the milling blank obtained in step vi and/or
   ix) securing of a pin on the surface of the milling blank so as to secure the milling blank in a milling machine.

3. Process for producing a dental milling blank according to any of the preceding aspects, wherein step iii is carried out by low-energy mixing.

4. Process for producing a dental milling blank according to any of the preceding aspects, wherein step iii is carried out by mixing in a shaker-mixer or a rotary mixer.

5. Process for producing a dental milling blank according to any of the preceding aspects, wherein step iii is carried out without a milling process and no milling additive is added.

6. Process for producing a dental milling blank according to any of the preceding aspects, wherein step iii is carried out without a milling process and no solvent as milling additive is added.

7. Process for producing a dental milling blank according to any of the preceding aspects, wherein step iii is carried out without a milling process and no milling medium is added.

8. Process for producing a dental milling blank according to any of the preceding aspects, wherein step iii is carried out without a milling process and no agate or zirconium dioxide beads as milling medium is added.

9. Process for producing a dental milling blank according to any of the preceding aspects, wherein step iii is carried out without a milling process and no milling additive and no milling medium is added.

10. Process for producing a dental milling blank according to any of the preceding aspects, wherein one or more colorants are added in one of steps i, ii or iii or wherein the liquid polymerizable composition (M) comprises colorants (D).

11. Process for producing a dental milling blank according to any of the preceding aspects that includes between steps v and vi a step v-a in which the compressed shaped article is immersed in a colorant solution.

12. Process for producing a dental milling blank according to any of the preceding aspects, wherein the colorant solution comprises colorants (D), polymerizable monomers (A), preferably (meth)acrylates and/or (meth)acrylamides, and optionally initiators.

13. Process for producing a dental milling blank according to any of the preceding aspects, in which steps i to iv are repeated one layer at a time and the powder layers compressed together in step v.

14. Process for producing a dental milling blank according to any of the preceding aspects, in which steps i to v are repeated one layer at a time, wherein each of the individual layers is differently colored by means of different colorants and/or by means of different amounts of colorant.

15. Process for producing a dental milling blank according to any of the preceding aspects, in which two or more differently colored surface-adsorbed powders $F_{sil,ads,1}$ to $F_{sil,ads,x}$ are each produced in parallel in steps i to iii and are in step vi filled, with mixing, into a mold, wherein the mixing ratio of $F_{sil,ads,1}$ to $F_{sil,ads,2}$ and to further $F_{sil,ads,x}$, if present, is altered during filling, preferably continuously altered.

16. Process for producing a dental milling blank according to any of the preceding aspects, wherein the compression in step v, which is preferably uniaxial or biaxial, is carried out at a pressure in the range from 400 to 12000 bar, preferably in the range from 2500 to 10000 bar, more preferably in the range from 4000 to 10 000 bar.

17. Process for producing a dental milling blank according to any of the preceding aspects, wherein the polymerization in step vi, which is preferably isostatic, is carried out at a pressure in the range from 50 to 750 bar, preferably in the range from 100 to 600 bar, more preferably in the range from 200 to 500 bar, and/or at a temperature in the range from 60 to 160° C., preferably in the range from 80 to 140° C.

18. Process for producing a dental milling blank according to any of the preceding aspects, wherein the compacting step v and the polymerizing step vi are carried out concomitantly at a temperature in the range from 60 to 160° C., preferably in the range from 80 to 140° C., through
   uniaxial or biaxial pressure in the range from 400 to 12000 bar, preferably in the range from 2500 to 10 000 bar, more preferably in the range from 4000 to 10 000 bar, or
   isostatic pressure in the range from 50 to 750 bar, preferably in the range from 100 to 600 bar, more preferably in the range from 200 to 500 bar.

19. Process for producing a dental milling blank according to any of the preceding aspects, wherein the inorganic filler powder (F) comprises one or more inorganic fillers selected from the group consisting of barium silicate glasses, barium aluminosilicate glasses, barium borosilicate silicate glasses, barium boroaluminosilicate glasses, barium fluoroboroaluminosilicate glasses, strontium silicate glasses, strontium aluminosilicate glasses, strontium borosilicate glasses, strontium boroaluminosilicate silicate glasses, strontium fluoroboroaluminosilicate glasses, zirconium silicate glasses, quartz, cristobalite, fumed silica and ytterbium fluoride, preferably selected from the group consisting of barium boroaluminosilicate silicate glasses, fumed silica and ytterbium fluoride.

20. Process for producing a dental milling blank according to any of the preceding aspects, wherein the inorganic filler powder F has a D50 value of from 0.18 to 10 µm, preferably from 0.4 to 5 µm.

21. Process for producing a dental milling blank according to any of the preceding aspects, wherein the inorganic filler powder F comprises a first inorganic filler powder F1 and a second inorganic filler powder F2.

22. Process for producing a dental milling blank according to any of the preceding aspects, wherein the first inorganic filler powder F1 and the second inorganic filler powder F2 may differ in their chemical composition and in their particle size.

23. Process for producing a dental milling blank according to any of the preceding aspects, wherein the first inorganic filler powder F1 has a D50 value of from 0.4 to 1.0 µm, preferably from 0.5 to 0.9 µm, and the second inorganic filler powder F2 has a D50 value of from 1.2 to 5.0 µm, preferably from 1.5 to 4.0 µm.

24. Process for producing a dental milling blank according to any of the preceding aspects, wherein the inorganic filler powder (F) contains at least 50% by weight, preferably at least 70% by weight, particularly preferably at least 90% by weight and very particularly preferably 100% by weight, of constituents capable of reacting with the silane $PG\text{-}L\text{-}Si(R^1)_n(OR^2)_{(3-n)}$.

25. Process for producing a dental milling blank according to any of the preceding aspects, wherein the polymerizable group PG of the silane $PG\text{-}L\text{-}Si(R^1)_n(OR^2)_{(3-n)}$ is selected from the group consisting of —OC(=O)CH=CH$_2$, —OC(=O)C(CH$_3$)=CH$_2$, —NHC(=O)CH=CH$_2$ and —NHC(=O)C(CH$_3$)=CH$_2$, preferably —OC(=O)CH=CH$_2$ and —OC(=O)C(CH$_3$)=CH$_2$, more preferably —OC(=O)C(CH$_3$)=CH$_2$.

26. Process for producing a dental milling blank according to any of the preceding aspects, wherein the linker group L of the silane $PG\text{-}L\text{-}Si(R^1)_n(OR^2)_{(3-n)}$ is an alkylene group having 1 to 12 carbon atoms, which may be interrupted by an oxygen atom or a urethane group.

27. Process for producing a dental milling blank according to any of the preceding aspects, wherein L is selected from the group consisting of —(CH$_2$)$_p$—, —(CH$_2$)$_q$—OC(=O)NH—(CH$_2$)$_p$— and —(CH$_2$)$_q$—NHC(=O)O—(CH$_2$)$_p$—, where p=1 to 8 and q=2 to 4.

28. Process for producing a dental milling blank according to any of the preceding aspects, wherein the silane $PG\text{-}L\text{-}Si(R^1)_n(OR^2)_{(3-n)}$ is selected from the group consisting of H$_2$C=C(CH$_3$)C(=O)O—(CH$_2$)$_p$—Si(OR$^2$)$_3$, H$_2$C=C(CH$_3$)C(=O)O—(CH$_2$)$_q$—NHC(=O)O—(CH$_2$)$_p$—Si(OR$^2$)$_3$ and H$_2$C=C(CH$_3$)C(=O)O—(CH$_2$)$_q$—OC(=O)NH—(CH$_2$)$_p$—Si(OR$^2$)$_3$, where R$^2$ is a C1 to C4 alkyl group, p=1 to 8 and q=2 to 4.

29. Process for producing a dental milling blank according to any of the preceding aspects, wherein the silane $PG\text{-}L\text{-}Si(R^1)_n(OR^2)_{(3-n)}$ is selected from the group consisting of H$_2$C=C(CH$_3$)C(=O)O—(CH$_2$)—Si(OR$^2$)$_3$, H$_2$C=C(CH$_3$)C(=O)O—(CH$_2$)$_3$—Si(OR$^2$)$_3$, H$_2$C=C(CH$_3$)C(=O)O—(CH$_2$)$_2$—NHC(=O)O—(CH$_2$)$_3$—Si(OR$^2$)$_3$ and H$_2$C=C(CH$_3$)C(=O)O—(CH$_2$)$_2$—OC(=O)NH—(CH$_2$)$_3$—Si(OR$^2$)$_3$, where R$^2$ is a C1 to C4 alkyl group.

30. Process for producing a dental milling blank according to any of the preceding aspects, wherein the silane $PG\text{-}L\text{-}Si(R^1)_n(OR^2)_{(3-n)}$ is 3-methacryloyloxypropyltrimethoxysilane.

31. Process for producing a dental milling blank according to any of the preceding aspects, wherein the liquid polymerizable composition (M) comprises
A) one, two or more polymerizable monomers, preferably (meth)acrylates and/or (meth)acrylamides,
B) an initiator or an initiator system, preferably a thermal initiator,
C) optionally inorganic, non-agglomerated, non-aggregated particles having an average particle size of less than 80 nm and
D) optionally colorants.

32. Process for producing a dental milling blank according to any of the preceding aspects, wherein the liquid polymerizable composition (M) comprises
A) in an amount of from 39% to 99% by weight, preferably 39% to 79% by weight, more preferably 39% to 59% by weight,
B) in an amount of from 0.5% to 5% by weight, preferably 0.5% to 3.0% by weight, more preferably 1.0% to 2.5% by weight,
C) in an amount of from 0% to 60% by weight, preferably 20% to 60% by weight, more preferably 40% to 60% by weight and
D) in an amount of from 0% to 1% by weight, preferably 0% to 0.5% by weight, more preferably 0.0001% to 0.1% by weight,
in each case based on the total mass of the liquid polymerizable composition (M).

33. Process for producing a dental milling blank according to any of the preceding aspects, wherein the proportion of polymerizable monomers (A) is 39% to 99% by weight, preferably 39% to 79% by weight, more preferably 39% to 59% by weight, based on the total mass of the liquid polymerizable composition (M).

34. Process for producing a dental milling blank according to any of the preceding aspects, wherein the polymerizable monomer (A) comprises one or more monomers selected from the group consisting of ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, neopentyl glycol di(meth)acrylate, butane-1,4-diol di(meth)acrylate, hexane-1,6-diol di(meth)acrylate, nonane-1,9-diol di(meth)acrylate, decane-1,10-diol di(meth)acrylate, dodecane-1,12-diol di(meth)acrylate, tricyclo[5.2.1.0$^{2,6}$]decane-3(4),8(9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5,12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl)carbamoylmethyl]-3-(2-(meth)acryloyloxyethyl)carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl-9'-ene)phenyl, 1,3-bis(1',1',9'-trimethyl-3',8'-dioxo-2'-aza-4',7'-dioxa-decyl-9'-ene)phenyl, 3(4),8(9)-bis(4',7'-dioxa-3',8'-dioxo-2'-aza-decyl-9'-ene)tetrahydrodicyclopentadiene, 3(4),8(9)-bis(4',7'-dioxa-3',8'-dioxo-2'-aza-9'-methyl-decyl-9'-ene)tetrahydrodicyclopentadiene, trimethylolpropane di(meth)acrylate, trimethylolpropane tri(meth)acrylate, ethoxylated trimethylolpropane tri(meth)acrylate, ditrimethylolpropane tetra(meth)acrylate, ethoxylated ditrimethylolpropane tetra(meth)acrylate, pentaerythritol di(meth)acrylate, pentaerythritol tri(meth)acrylate, pentaerythritol tetra(meth)acrylate, dipentaerythritol tetra(meth)acrylate, dipentaerythritol penta(meth)acrylate, dipentaerythritol hexa(meth)acrylate, 2,2-bis[4-[3-(meth)acryloyloxy-2-hydroxypropoxy]phenyl]propane, 2,2-bis[4-[2-(meth)acryloyloxy-3-hydroxypropoxy]phenyl]propane, ethoxylated bisphenol A di(meth)acrylate, propoxylated bisphenol A di(meth)acrylate, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane, 2-[4-(meth)acryloyloxdipropoxyphenyl]-2-[4-(meth)acryloyloxytriethoxyphenyl]propane, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, methyl (meth)acrylate, ethyl (meth)acrylate, propyl (meth)acrylate, butyl (meth)acrylate, hexyl (meth)acrylate, 2-ethylhexyl (meth)acrylate, tetrahydrofurfuryl (meth)acrylate, isobornyl (meth)acrylate, lauryl (meth)acrylate, cyclohexyl (meth)acrylate, (octahydro-4,7-methano-1H-indenyl)methyl (meth)acrylate, benzyl (meth)acrylate and phenoxyethyl (meth)acrylate, preferably selected from the group consisting of triethylene glycol di(meth)acrylate, tetraethylene glycol di(meth)acrylate, hexane-1,6-diol di(meth)acrylate, decane-1,10-diol di(meth)acrylate, dodecane-1,12-diol di(meth)acrylate, tricyclo[5.2.1.0$^{2,6}$]decane-3(4),8(9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5,12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl)carbamoylmethyl]-3-(2-(meth)acryloyloxyethyl)carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl-9'-ene)phenyl, 1,3-bis(1',1',9'-trimethyl-3',8'-dioxo-2'-aza-4',7'-dioxa-decyl-9'-ene)phenyl, 3(4),8(9)-bis(4',7'-dioxa-3',8'-dioxo-2'-aza-decyl-9'-ene)tetrahydrodicyclopentadiene, 3(4),8(9)-bis(4',7'-dioxa-3',8'-dioxo-2'-aza-9'-methyl-decyl-9'-ene)tetrahydrodicyclopentadiene, 2,2-bis[4-[3-(meth)acryloyloxy-2-hydroxypropoxy]phenyl]propane, 2,2-bis[4-[2-(meth)acryloyloxy-3-hydroxypropoxy]phenyl]propane, ethoxylated bisphenol A di(meth)acrylate, propoxylated bisphenol A di(meth)acrylate, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane and 2-[4-(meth)acryloyloxdipropoxyphenyl]-2-[4-(meth)acryloyloxytriethoxyphenyl]propane.

35. Process for producing a dental milling blank according to any of the preceding aspects, wherein the proportion of initiators (B) is 0.5% to 5% by weight, preferably 0.5% to 3.0% by weight, more preferably 1.0% to 2.5% by weight, based on the total mass of the liquid polymerizable composition (M).

36. Process for producing a dental milling blank according to any of the preceding aspects, wherein the initiator or the initiator system (B) is selected from the group consisting of ketone peroxides, peroxyketals, hydroperoxides, dialkyl peroxides, diacyl peroxides, peroxyesters, peroxydicarbonates and azo compounds.

37. Process for producing a dental milling blank according to any of the preceding aspects, wherein the initiator (B) is selected from the group consisting of dibenzoyl peroxide, bis(2,4-dichlorobenzoyl) peroxide, dilauroyl peroxide, dicumyl peroxide, tert-butyl perbenzoate, cumene hydroperoxide, tert-butyl peroxy-3,5,5-trimethylhexanoate, 2,2'-azobisisobutyronitrile, 2,2'-azobis(2-methylbutyronitrile), 2,2'-azobis-2,4-dimethylvaleronitrile, 2,2'-azobis-1-cyclohexanecarbonitrile and dimethyl 2-2'-azobisisobutyrate, preferably selected from the group consisting of dibenzoyl peroxide, bis(2,4-dichlorobenzoyl) peroxide, dilauroyl peroxide and 2,2'-azobisisobutyronitrile, more preferably dibenzoyl peroxide.

38. Process for producing a dental milling blank according to any of the preceding aspects, wherein the proportion of inorganic, non-agglomerated, non-aggregated particles (C) is 0% to 60% by weight, preferably 20% to 60% by weight, more preferably 40% to 60% by weight, based on the total mass of the liquid polymerizable composition (M).

39. Process for producing a dental milling blank according to any of the preceding aspects, wherein the inorganic, non-agglomerated, non-aggregated particles (C) have an average particle size determined by DLS with a volume-weighted D50 value of less than 80 nm, preferably 8 to 80 nm, more preferably from 10 to 60 nm.

40. Process for producing a dental milling blank according to any of the preceding aspects, wherein the inorganic, non-agglomerated, non-aggregated particles (C) are present in a monodisperse and completely dispersed form.

41. Process for producing a dental milling blank according to any of the preceding aspects, wherein the inorganic, non-agglomerated, non-aggregated particles (C) are $SiO_2$ and/or $YbF_3$ particles.

42. Process for producing a dental milling blank according to any of the preceding aspects, wherein the inorganic, non-agglomerated, non-aggregated particles (C) are $SiO_2$ particles and are surface-coated with a silane of formula PG-L-Si($R^1$)$_n$(O$R^2$)$_{(3-n)}$, preferably with 3-methacryloxypropyltrimethoxysilane.

43. Process for producing a dental milling blank according to any of the preceding aspects, wherein the inorganic, non-agglomerated, non-aggregated particles (C) are $YbF_3$ particles and are surface-coated with 10-[(2-methylprop-2-enoyl)oxy]decyl dihydrogen phosphate.

44. Process for producing a dental milling blank according to any of the preceding aspects, wherein the proportion of colorants (D) is 0% to 1% by weight, preferably 0% to 0.5% by weight, more preferably 0.0001% to 0.1% by weight, in each case based on the total mass of the liquid polymerizable composition (M).

45. Process for producing a dental milling blank according to any of the preceding aspects, wherein the colorants (D) are inorganic color pigments, organic color pigments or dyes.

46. Process for producing a dental milling blank according to any of the preceding aspects, wherein the colorants (D) are inorganic color pigments selected from the group consisting of iron oxide, titanium dioxide, barium sulfate and aluminum oxide.

47. Process for producing a dental milling blank according to any of the preceding aspects, wherein the colorants (D) comprise organic dyes that are dissolved in the liquid polymerizable composition (M) and added therewith in step iii.

48. Process for producing a dental milling blank according to any of the preceding aspects, wherein the colorants (D) comprise inorganic or organic color pigments that are dispersed in the liquid polymerizable composition (M) and added therewith in step iii.

49. Process for producing a dental milling blank according to any of the preceding aspects, wherein the mass ratio of surface-coated powder ($F_{sil}$) to liquid polymerizable composition (M) is in the range from 3:1 to 10:1, preferably in the range from 4:1 to 9:1 and more preferably in the range from 5:1 to 8:1.

50. Process for producing a dental milling blank according to any of the preceding aspects, wherein the total filler content, i.e. the sum total of the mass fractions of the surface-coated powder ($F_{sil}$) and of the inorganic, non-agglomerated, non-aggregated particles (C), if present, is in the range from 80% by weight to 95% by weight, preferably in the range from 83% by weight to 94% by weight and more preferably in the range from 85% by weight to 93% by weight, in each case based on the total mass of the milling blank.

51. Dental milling blank produced in a process according to any of the preceding aspects.

52. Dental milling blank produced by compressing and polymerizing an inorganic filler powder ($F_{sil,ads}$), on the surface of which is present
    a coating with a silane (S) PG-L-Si($R^1$)$_n$(O$R^2$)$_{(3-n)}$, where PG is a polymerizable group, L is a linker group that links the polymerizable group PG to the silicon atom, $R^1$ is a C1 to C4 alkyl group or phenyl group, $R^2$ is a C1 to C4 alkyl group or a hydrogen atom and n=0, 1 or 2,
    and
    a liquid polymerizable composition (M) adsorbed thereon, comprising
    (A) one, two or more polymerizable monomers, preferably (meth)acrylates and/or (meth)acrylamides,
    (B) an initiator or an initiator system, preferably a thermal initiator,
    (C) optionally inorganic, non-agglomerated, non-aggregated particles having an average particle size of less than 80 nm and
    (D) optionally colorants.

53. Kit comprising a plurality of milling blanks produced in a process according to any of aspects 1 to 50, wherein the milling blanks
    have the same monochrome color or
    have different monochrome colors or
    have the same layered color gradation or
    have the same continuous color gradation.

54. Kit comprising
    a plurality of milling blanks produced in a process according to any of aspects 1 to 50,
    a conditioning agent for indirect restorations produced from the milling blanks and
    a luting material for luting indirect restorations produced from the milling blanks.

The invention claimed is:

1. A process for producing a dental milling blank comprising the following steps:
   i) producing or providing an inorganic filler powder (F),
   ii) at least partial coating of the surface of the inorganic filler powder (F) by reaction with a silane(S) of formula PG-L-Si($R^1$)$_n$(O$R^2$)$_{(3-n)}$ where PG is a polymerizable group,
   L is a linker group that links the polymerizable group PG to the silicon atom
   $R^1$ is a $C_1$ to $C_4$ alkyl group or phenyl group,
   $R^2$ is a $C_1$ to $C_4$ alkyl group or a hydrogen atom,
   n=0, 1 or 2,
   wherein a surface-coated powder ($F_{sil}$) is obtained,
   iii) adsorbing on the surface of the filler powder obtained in step ii ($F_{sil}$) of a liquid polymerizable composition (M), capable of polymerizing with the polymerizable group PG, wherein a surface-adsorbed powder ($F_{sil,ads}$) is obtained,
   iv) filling of the powder obtained in step iii ($F_{sil,ads}$) into a mold,
   v) compressing of the powder ($F_{sil}$, ads) in the mold under pressure and
   vi) polymerizing of the polymerizable composition M and of the polymerizable groups PG.

2. The process for producing a dental milling blank according to claim 1, wherein the process additionally comprises one or more of the following steps:
   vii) demolding of the milling blank obtained in step vi and/or
   viii) further processing of the milling blank obtained in step vi and/or
   ix) securing of a pin on the surface of the milling blank so as to secure the milling blank in a milling machine.

3. The process for producing a dental milling blank according to claim 1, wherein the compression in step v is carried out at a pressure in the range from 400 to 12000 bar.

4. The process for producing a dental milling blank according to claim 1, wherein the polymerization in step vi is carried out at a pressure in the range from 50 to 750 bar and/or at a temperature in the range from 60 to 160° C.

5. The process for producing a dental milling blank according to claim 1, wherein the compacting step v and the polymerizing step vi are carried out concomitantly at a temperature in the range from 60 to 160° C. through
uniaxial or biaxial pressure in the range from 400 to 12000 bar,
or
isostatic pressure in the range from 50 to 750 bar.

6. The process for producing a dental milling blank according to claim 1, wherein the polymerizable group PG of the silane(S) is selected from the group consisting of —OC(=O)CH=CH$_2$, —OC(=O)C(CH$_3$)=CH$_2$, —NHC(=O)CH=CH$_2$ and —NHC(=O)C(CH$_3$)=CH$_2$.

7. The process for producing a dental milling blank according to claim 1, wherein the linker group L of the silane(S) is an alkylene group having 1 to 12 carbon atoms, which may be interrupted by an oxygen atom or a urethane group.

8. The process for producing a dental milling blank according to claim 1, wherein the inorganic filler powder (F) comprises one or more inorganic fillers selected from the group consisting of barium silicate glasses, barium aluminosilicate glasses, barium borosilicate silicate glasses, barium boroaluminosilicate glasses, barium fluoroboroaluminosilicate glasses, strontium silicate glasses, strontium aluminosilicate glasses, strontium borosilicate glasses, strontium boroaluminosilicate silicate glasses, strontium fluoroboroaluminosilicate glasses, zirconium silicate glasses, quartz, cristobalite, fumed silica and ytterbium fluoride.

9. The process for producing a dental milling blank according to claim 1, wherein the inorganic filler powder F has a D50 value of from 0.18 to 10 µm.

10. The process for producing a dental milling blank according to claim 1, wherein the inorganic filler powder F comprises a first inorganic filler powder F1 and a second inorganic filler powder F2.

11. The process for producing a dental milling blank according to claim 10, wherein the first inorganic filler powder F1 has a D50 value of from 0.4 to 1.0 µm and the second inorganic filler powder F2 has a D50 value of from 1.2 to 5.0 µm.

12. The process for producing a dental milling blank according to claim 1, wherein the liquid polymerizable composition (M) comprises
A) one, two or more polymerizable monomers,
B) an initiator or an initiator system,
C) optionally inorganic, non-agglomerated, non-aggregated particles having an average particle size of less than 80 nm and
D) optionally colorants.

13. The process for producing a dental milling blank according to claim 12, wherein the polymerizable monomer (A) comprises one or more monomers selected from the group consisting of ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, neopentyl glycol di(meth)acrylate, butane-1,4-diol di(meth)acrylate, hexane-1,6-diol di(meth)acrylate, nonane-1,9-diol di(meth)acrylate, decane-1,10-diol di(meth)acrylate, dodecane-1,12-diol di(meth)acrylate, tricyclo[5.2.1.0$^{2,6}$]decane-3 (4),8 (9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5,12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl) carbamoylmethyl]-3-(2-(meth)acryloyloxyethyl) carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl-9'-ene)phenyl, 1,3-bis(1',1',9'-trimethyl-3',8'-dioxo-2'-aza-4',7'-dioxa-decyl-9'-ene)phenyl, 3 (4),8 (9)-bis(4',7'-dioxa-3',8'-dioxo-2'-aza-decyl-9'-ene) tetrahydrodicyclopentadiene, 3 (4),8 (9)-bis(4',7'-dioxa-3',8'-dioxo-2'-aza-9'-methyl-decyl-9'-ene) tetrahydrodicyclopentadiene, trimethylolpropane di(meth)acrylate, trimethylolpropane tri(meth)acrylate, ethoxylated trimethylolpropane tri(meth)acrylate, ditrimethylolpropane tetra(meth)acrylate, ethoxylated ditrimethylolpropane tetra (meth)acrylate, pentaerythritol di(meth)acrylate, pentaerythritol tri(meth)acrylate, pentaerythritol tetra(meth)acrylate, dipentaerythritol tetra(meth)acrylate, dipentaerythritol penta (meth)acrylate, dipentaerythritol hexa(meth)acrylate, 2,2-bis[4-[3-(meth)acryloyloxy-2-hydroxypropoxy]phenyl]propane, 2,2-bis[4-[2-(meth)acryloyloxy-3-hydroxypropoxy] phenyl]propane, ethoxylated bisphenol A di(meth)acrylate, propoxylated bisphenol A di(meth)acrylate, 2,2-bis[4-(meth)acryloyloxyethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane, 2-[4-(meth)acryloyloxdipropoxyphenyl]-2-[4-(meth)acryloyloxytriethoxyphenyl]propane, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, methyl (meth)acrylate, ethyl (meth)acrylate, propyl (meth)acrylate, butyl (meth)acrylate, hexyl (meth)acrylate, 2-ethylhexyl (meth)acrylate, tetrahydrofurfuryl (meth)acrylate, isobornyl (meth)acrylate, lauryl (meth)acrylate, cyclohexyl (meth) acrylate, (octahydro-4,7-methano-1H-indenyl)methyl (meth)acrylate, benzyl (meth)acrylate and phenoxyethyl (meth)acrylate, preferably selected from the group consisting of triethylene glycol di(meth)acrylate, tetraethylene glycol di(meth)acrylate, hexane-1,6-diol di(meth)acrylate, decane-1,10-diol di(meth)acrylate, dodecane-1,12-diol di(meth)acrylate, tricyclo[5.2.1.0$^{2,6}$]decane-3 (4),8 (9)-dimethanol di(meth)acrylate, 2-hydroxypropyl 1,3-di(meth)acrylate, 3-hydroxypropyl 1,2-di(meth)acrylate, urethane di(meth)acrylate, 7,7,9-trimethyl-3,14-dioxa-4,13-dioxo-5, 12-diazahexadecane-1,16-diyl di(meth)acrylate, 7,9,9-trimethyl-3,14-dioxa-4,13-dioxo-5,12-diazahexadecane-1,16-diyl di(meth)acrylate, 1,5,5-trimethyl-1-[(2-(meth)acryloyloxyethyl) carbamoylmethyl]-3-(2-(meth)acryloyloxyethyl) carbamoylcyclohexane, 1,3-bis(3',8'-dioxo-2'-aza-4',7'-dioxa-decyl-9'-ene)phenyl, 1,3-bis(9'-methyl-3',8'-dioxo-2'-aza-4',7'-dioxa-decyl-9'-ene)phenyl, 1,3-bis(1',1'-dimethyl-3',8'-dioxo-2'-aza-4',7'-dioxa-decyl- 9'-ene)phenyl, 1,3-bis(1',1',9'-trimethyl-3',8'-dioxo-2'-aza-4',7'-dioxa-decyl-9'-ene)phenyl, 3 (4), 8 (9)-bis(4',7'-dioxa-3',8'-dioxo-2'-aza-decyl-9'-ene) tetrahydrodicyclopentadiene, 3 (4),8 (9)-bis(4',7'-dioxa-3', 8'-dioxo-2'-aza-9'-methyl-decyl-9'-ene) tetrahydrodicyclopentadiene, 2,2-bis[4-[3-(meth)acryloyloxy-2-hydroxypropoxy]phenyl]propane, 2,2-bis[4-[2-(meth)acryloyloxy-3-hydroxypropoxy]phenyl]propane, ethoxylated bisphenol A di(meth)acrylate, propoxylated bisphenol A di(meth)acrylate, 2,2-bis[4-(meth)acryloyloxy-ethoxyphenyl]propane, 2,2-bis[4-(meth)acryloyloxydiethoxyphenyl]propane, 2,2-bis[4-(meth)acryloyloxytriethoxyphenyl]propane, 2,2-bis[4-(meth)acryloyloxytetraethoxyphenyl]propane, 2,2-bis[4-(meth)acryloyloxypentaethoxyphenyl]propane, 2,2-bis[4-(meth)acryloyloxydipropoxyphenyl]propane, 2,2-bis[4-(meth)acryloyloxyethoxyphenyl]-2-[4-(meth)acryloyloxydiethoxyphenyl]propane, 2-[4-(meth)acryloyloxydiethoxyphenyl]-2-[4-(meth)acryloyloxytriethoxyphenyl]propane and 2-[4-(meth)acryloyloxdipropoxyphenyl]-2-[4-(meth)acryloyloxytriethoxyphenyl]propane.

14. The process for producing a dental milling blank according to claim 12, wherein the initiator (B) is selected from the group consisting of dibenzoyl peroxide, bis(2,4-dichlorobenzoyl) peroxide, dilauroyl peroxide, dicumyl peroxide, tert-butyl perbenzoate, cumene hydroperoxide, tert-butyl peroxy-3,5,5-trimethylhexanoate, 2,2'-azobisisobutyronitrile, 2,2'-azobis(2-methylbutyronitrile), 2,2'-azobis-2,4-dimethylvaleronitrile, 2,2'-azobis-1-cyclohexanecarbonitrile and dimethyl 2-2'-azobisisobutyrate.

15. The process for producing a dental milling blank according to claim 12, wherein the colorants (D) are selected from the group consisting of inorganic color pigments, organic color pigments and dyes, and/or wherein the colorants (D) are inorganic color pigments selected from the group consisting of iron oxide, titanium dioxide, barium sulfate and aluminum oxide.

16. The process for producing a dental milling blank according to claim 1, wherein one or more colorants are added in one of steps i, ii or iii or wherein the liquid polymerizable composition (M) comprises colorants (D).

17. The process for producing a dental milling blank according to claim 1,
in which steps i to iv are repeated one layer at a time and the powder layers compressed together in step v or in which steps i to v are repeated one layer at a time, wherein each of the individual layers is differently colored by means of different colorants and/or by means of different amounts of colorant;
or
in which two differently colored surface-adsorbed powders $F_{sil,ads,1}$ and $F_{sil,ads,2}$ are each produced in parallel in steps i to iii and are in step vi filled, with mixing, into a mold, wherein the mixing ratio of $F_{sil,ads,1}$ to $F_{sil,ads,2}$ is altered during filling.

18. The process of claim 12, comprising:
the polymerizable monomer (A) in an amount of from 39% to 99% by weight;
the initiator or initiation system (B) in an amount of from 0.5% to 5% by weight;
the inorganic, non-agglomerated, non-aggregated particles (C) having an average particle size of less than 80 nm in an amount of from 0% to 60% by weight; and
the colorants (D) in an amount of from 0% to 1% by weight;
in each case based on the total mass of the liquid polymerizable composition (M).

\* \* \* \* \*